(12) United States Patent
Koo

(10) Patent No.: US 11,759,194 B1
(45) Date of Patent: Sep. 19, 2023

(54) SYSTEMS AND METHODS FOR COMBINED PERIOCULAR DIRECT-ILLUMINATION AND TRANS-CONJUNCTIVAL AND TRANS-SCLERAL RETRO-ILLUMINATION DURING OPHTHALMIC SURGERY

(71) Applicant: Edward Y. Koo, Hillsborough, CA (US)

(72) Inventor: Edward Y. Koo, Hillsborough, CA (US)

( * ) Notice: Subject to any disclaimer, the term of this patent is extended or adjusted under 35 U.S.C. 154(b) by 0 days.

(21) Appl. No.: 17/717,252

(22) Filed: Apr. 11, 2022

Related U.S. Application Data

(63) Continuation of application No. 16/195,422, filed on Nov. 19, 2018, now Pat. No. 11,298,118.

(51) Int. Cl.
*A61B 17/02* (2006.01)
*A61B 90/30* (2016.01)

(52) U.S. Cl.
CPC ...... *A61B 17/0231* (2013.01); *A61B 17/0206* (2013.01); *A61B 2090/309* (2016.02)

(58) Field of Classification Search
CPC .................................................. A61B 17/0231
See application file for complete search history.

(56) References Cited

U.S. PATENT DOCUMENTS

| | | | |
|---|---|---|---|
| 3,680,546 A * | 8/1972 | Asrican | A61B 3/0008 600/245 |
| 4,037,589 A | 7/1977 | McReynolds | |
| 5,054,906 A | 10/1991 | Lyons, Jr. | |
| 5,070,860 A | 12/1991 | Grounauer | |
| 5,171,254 A | 12/1992 | Sher | |
| 5,695,492 A | 12/1997 | Brown | |
| 6,267,752 B1 | 7/2001 | Svetliza | |

(Continued)

FOREIGN PATENT DOCUMENTS

WO    WO 2016/062398    4/2016

OTHER PUBLICATIONS

Philipp Simon Kolbl et al. "An extraocular non-invasive transscleral LED-endoilluminator for eye speculum integration" Published online: May 10, 2015.

(Continued)

*Primary Examiner* — Tessa M Matthews

(57) ABSTRACT

Systems and methods are provided for illumination of the periorbital exterior of the eye and the interior of the eye with a non-invasive (or non-penetrating), trans-corneal, trans-conjunctival, trans-scleral, non-incandescent, and/or low-temperature light source. In some examples a ring structure is configured to sit on a surface area of an eye, the ring structure having a top surface and a bottom surface, wherein the bottom surface is configured to touch the eye. A plurality of light-emitting elements is configured in the ring structure and a plurality of apertures is configured on the bottom surface of the ring structure, wherein the plurality of light-emitting elements is aligned with the plurality of apertures. A signal carrier runs along at least a portion of the ring structure, the signal carrier having one end configured to connect to a signal source and receive at least one of light and electricity from the signal source, and one or more opposite ends respectively coupled with the plurality of light-emitting elements.

18 Claims, 13 Drawing Sheets

BOTTOM VIEW

(56) References Cited

U.S. PATENT DOCUMENTS

| | | |
|---|---|---|
| 2007/0159600 A1 | 7/2007 | Gil et al. |
| 2012/0310141 A1* | 12/2012 | Kornfield .............. A61F 9/0008 |
| | | 604/20 |
| 2020/0163737 A1* | 5/2020 | Singh ..................... A61B 90/30 |
| 2020/0178964 A1 | 6/2020 | Khristov |
| 2022/0071615 A1* | 3/2022 | Zacharia ................ A61B 90/30 |

OTHER PUBLICATIONS

William F. Wiley, Md "The iLight Speculum", Apr. 2018| Insert To Cataract & Refractive Surgery Today.

* cited by examiner

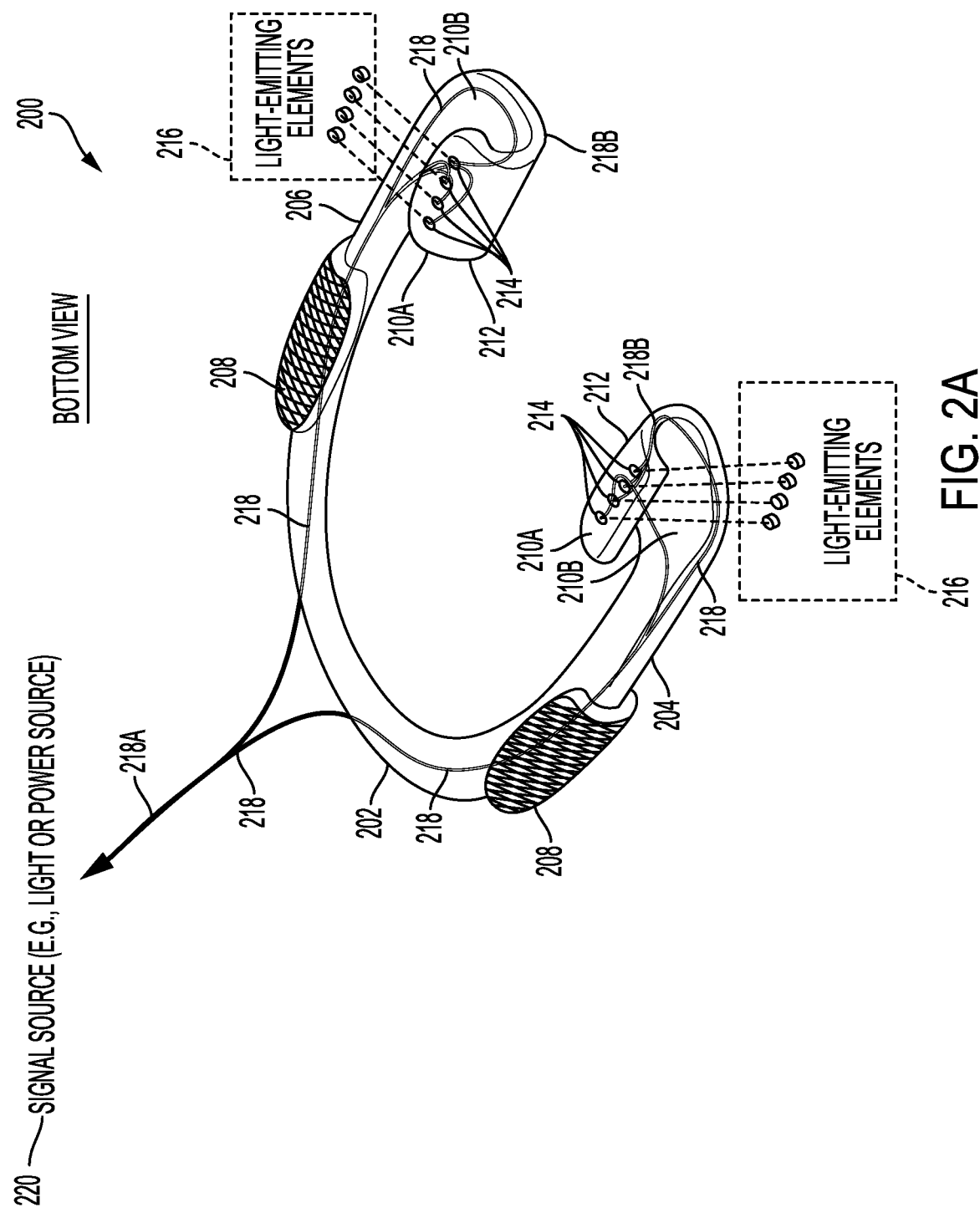

BOTTOM VIEW

BOTTOM VIEW

SYSTEMS AND METHODS FOR COMBINED PERIOCULAR DIRECT-ILLUMINATION AND TRANS-CONJUNCTIVAL AND TRANS-SCLERAL RETRO-ILLUMINATION DURING OPHTHALMIC SURGERY

TECHNICAL FIELD

The present technology pertains to ophthalmic surgery devices, and more specifically to combined periocular direct-illumination and trans-conjunctival and trans-scleral retro-illumination during ophthalmic surgery.

BACKGROUND

The human eye is susceptible to various conditions that are treatable through surgery and similar procedures. One such condition is cataracts, which refers to a condition where the lens of the eye becomes cloudy due to protein build-up in the lens of the eye over time. This reduces or even prevents light from passing clearly through the lens of the eye and can cause a significant decrease in vision. To improve or restore clear vision, cataracts can be removed through a surgical procedure.

To remove a cataract, a surgeon performs cataract surgery using a microscope. The surgeon first makes several small incisions of about a few millimeters or so in length in the cornea. The surgeon then inserts microsurgical instruments through the incisions to remove the cataract. During such surgical procedures, proper illumination of the inside of the eye is important. Typically, the microscope projects two powerful light beams to illuminate the anterior and posterior segments of the eye. A light source, such as a halogen tungsten lamp or high-pressure arc lamp (e.g., metal-halides, Xe, etc.), may be used to produce the light. The light passes through several optical elements (typically lenses, mirrors, and attenuators), and is transmitted to the eye.

One light beam is generally more diffuse and used to illuminate the cornea and anterior segment. A second light beam, which is generally more focused, is projected through the dilated pupil and subsequently reflected off the retina in the posterior segment, transmitted back through the dilated pupil and observed as a red reflex. The red reflex enables proper visualization of the lens and lens capsule. Without the red reflex, it would be very difficult to perform cataract surgery, as the lens and lens capsule would appear black compared to the well-illuminated cornea and iris structures. Thus, the surgical microscope can provide both illumination and magnification for cataract surgery. Unfortunately, the cost of surgical microscopes is extremely high, which consequently raises the cost of cataract surgery and similar procedures significantly and even renders such procedures unfeasible or inaccessible to many in need, particularly in remote and low-income areas of the world.

BRIEF DESCRIPTION OF THE DRAWINGS

In order to describe the manner in which the above-recited and other advantages and features can be obtained, a more particular description will be rendered by reference to specific implementations thereof which are illustrated in the appended drawings. Understanding that these drawings depict only example implementations of the disclosure and are not therefore to be considered to be limiting of its scope, the principles herein will be described and explained with additional specificity and detail through the use of the accompanying drawings in which:

FIGS. 2A through 2C illustrate example configurations of a speculum, in accordance with various embodiments;

DETAILED DESCRIPTION

Figure 1:
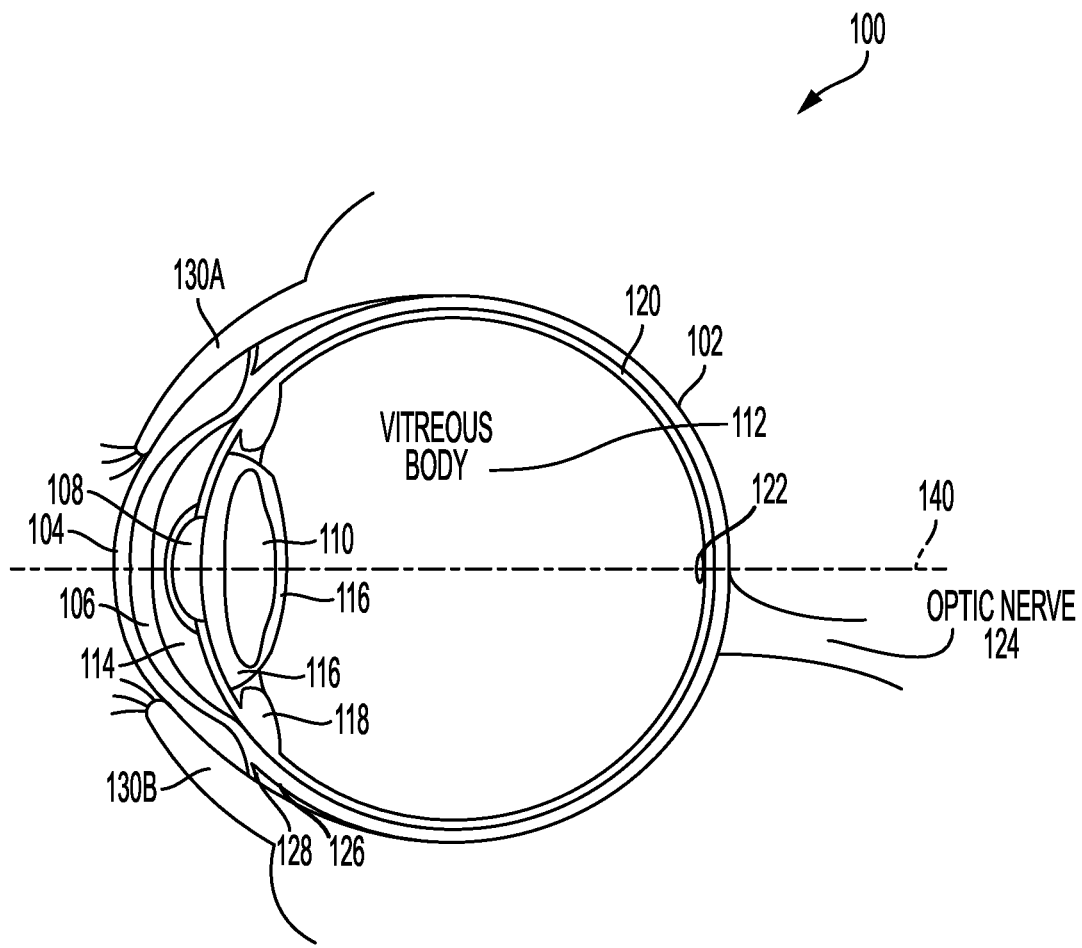
FIG. 1 illustrates an example eye system, in accordance with various embodiments.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description.

References to one or an embodiment in the present disclosure can refer to the same embodiment or any disclosed embodiment. For example, reference to "one embodiment", "an embodiment" or "some embodiments" means that any features, concepts, structures, and/or characteristics described in connection with such embodiment(s) are included in at least such embodiment(s) of the disclosure, but are not limited to such embodiment(s) and can indeed be included in any other embodiment(s) of the disclosure. The appearances of the phrases "in one embodiment", "in an embodiment" or "in some embodiments" in various places in the disclosure are not necessarily all referring to the same embodiment(s), nor are separate or alternative embodiments mutually exclusive of other embodiments.

The terms used in this specification generally have their ordinary meanings in the art, within the context of the disclosure, and in the specific context where each term is used. Unless otherwise defined, technical and scientific terms used herein have the meaning as commonly understood by one of ordinary skill in the art to which this disclosure pertains. In the case of conflict, the present document, including definitions and description will control.

Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms.

The use of examples anywhere in this specification including examples of any terms discussed herein is illustrative only, and is not intended to further limit the scope and meaning of the disclosure or of any example term. Note that titles or subtitles may be used in the examples for convenience of a reader, which in no way should limit the scope of the disclosure.

Without intent to limit the scope of the disclosure, examples of instruments, apparatus, methods and their related results according to embodiments of the present disclosure are given below. However, the disclosure is not limited to the examples or embodiments described in this specification. Additional features and advantages of the disclosure will be set forth in the description which follows, and in part will be obvious from the description, or can be learned by practice of the principles disclosed herein. The features and advantages of the disclosure can be realized and obtained by means of the instruments, elements and techniques particularly pointed out in the appended claims. These and other features of the disclosure will become more fully apparent from the following description and appended claims, and/or can be learned by the practice of the principles set forth herein.

OVERVIEW

The technologies herein allow proper illumination, including simultaneous anterior segment and posterior segment red reflex, to be provided in a low-cost, compact device and enable surgeons to utilize lower cost wearable loupes and the like to safely perform eye procedures, such as cataract surgery. The technologies herein therefore enable surgeons to safely perform eye procedures, including surgery, without the need of expensive—and often unaffordable—microscopes. The technologies herein also make the surgical light and magnification system "backpack" portable, thus affording significant savings in the cost of expensive equipment previously required for intraocular surgery and procedures, and consequently increases the access of such eye procedures around the world, particularly in remote and low-income areas where such procedures were previously inaccessible. The technologies herein also provide illumination devices and techniques for increased clarity and illumination of the eye, which further reduce or eliminate the risk of damage to the eye from thermal and phototoxic injuries common in prior art technologies.

Disclosed are systems, methods, and computer-readable media for providing combined illumination of both the periorbital exterior of the eye (e.g., the eyelids, cornea, conjunctiva and sclera) and the interior of the eye (e.g., the iris, lens, capsule, vitreous and retina) with a non-invasive (or non-penetrating), trans-corneal, trans-conjunctival, trans-scleral, non-incandescent, and/or low-temperature light source. In some cases, at least part of the light source can be positioned between the limbus and/or up to 12 millimeters (mm) or so posteriorly, to achieve retro-illumination. The light source can be directly placed on the conjunctival tissue or transmitted indirectly to the conjunctival tissue surface via a light carrier such as an optical fiber cable. In some cases, the light can be sufficiently powerful to trans-illuminate through all layers of the eye wall (e.g., the conjunctiva, sclera, choroid and retina). The light source can be powered by one or more energy sources, such as, without limitation, a portable and/or self-contained energy source (e.g., lithium batteries, NiCad batteries, etc.). In some cases, the energy source(s) can be recharged with a manual device, such as a rotating handle, a generator, or any other charging mechanism or device.

In some implementations, a speculum is provided including a first speculum arm having one or more blades located at a distal end of the first speculum arm, and a second speculum arm having one or more blades located at the distal end of the second speculum arm. The speculum can include a first set of light-emitting elements (e.g., light-emitting diodes, fiber optic elements, etc.) located on the one or more blades at the first speculum arm, and a second set of light-emitting elements located on the one or more blades at the second speculum arm. The first and second sets of light-emitting elements can be configured to provide illumination to one or more areas of an eye structure, and can be inserted/integrated into and/or contained within apertures or openings in the one or more blades.

The speculum can also include a signal carrier (e.g., electrical wire, fiber optic cable, etc.) running along at least a portion of the first speculum arm and the second speculum arm. The signal carrier can have one end configured to connect to a signal source (e.g., a power source, a light source, etc.) and receive light and/or electricity from the signal source. The signal carrier can also have one or more ends (e.g., one or more ends opposite to the end connected to the signal source) respectively coupled with the first and second sets of light-emitting elements. The signal carrier can receive and transmit the light and/or electricity from the signal source to the first and second sets of light-emitting elements to emit light.

The speculum can also include one or more additional illumination devices for additional illumination of the eye. For example, the speculum can include one or more adjustable illumination devices secured, fastened, attached, coupled, and/or positioned on the speculum for providing additional light. The illumination devices can include, for example, a light-emitting diode (LED), a fiber optic element (e.g., fiber optic cable, filament, strand, fiber, point, end, etc.), and so forth. The illumination devices can couple with, or connect to, the signal carrier to receive light and/or electricity from the signal source.

In some implementations, an apparatus is provided for eye illumination during eye procedures. The apparatus can include a ring structure configured to sit on a surface area of an eye. The ring structure can include a plurality of apertures configured to receive a plurality of light-emitting elements (e.g., LEDs, fiber optics, etc.). In some cases, the plurality of apertures can be on an inside surface of the ring structure, and the plurality of light-emitting elements can be installed on the plurality of apertures with a light-emitting end facing away from the inner surface of the ring structure. In some cases, the plurality of light-emitting elements can be positioned at least partially within the plurality of apertures. Moreover, the plurality of light-emitting elements can be configured to provide illumination to one or more areas of the eye from a location at least partially within the plurality of apertures.

The ring structure can include a signal carrier (e.g., electrical wire, fiber optic cable, etc.) running along at least a portion of the ring structure. The signal carrier can have one end configured to connect to a signal source (e.g., power and/or light source) and receive light and/or electricity from the signal source. The signal carrier can have one or more other ends (e.g., one or more ends opposite to the end connected to the signal source) respectively coupled with the plurality of light-emitting elements. The signal carrier can receive and transmit the light and/or electricity from the signal source to the plurality of light-emitting elements.

In some examples, the ring structure can also include one or more adjustable illumination devices (e.g., LEDs, fiber optics, etc.) positioned at one or more locations on the ring structure and connected to, or coupled with, the signal carrier. The signal carrier can receive and transmit light and/or electricity from the signal source to the one or more illumination devices, which can use such light and/or electricity to generate and/or output light.

In other implementations, a standalone apparatus is provided for eye illumination during eye procedures. The apparatus can include a standalone light head having a light output port configured to emit light, and one or more attaching elements (e.g., rotational barbs) configured to secure or fasten the standalone light head to one or more surfaces of an eye. The apparatus can include a signal carrier (e.g., an electrical wire, a fiber optic cable, etc.) having a first end coupled with the standalone light head (and/or the light output port) and a second end connected to a signal source (e.g., a power and/or light source). The signal carrier can be configured to transmit electricity and/or light from the signal source to the standalone light head, which the light output port can then use to emit light.

In some cases, the light output port can include an LED and/or a fiber optic cable output portion. When the light output port includes an LED, the signal carrier can include an electrical wire for transmitting electricity to the LED. When the light output port includes a fiber optic element, the signal carrier can include a fiber optic cable for transmitting light to the fiber optic cable output portion.

Description of Example Embodiments

The present technology will be described in the following disclosure as follows. The discussion begins with a description of a mammalian eye system, as shown in FIG. 1. A discussion of example systems, methods, and technologies for providing combined illumination of both the periorbital exterior of the eye and the interior of the eye, as shown in FIGS. 2A through 10, will then follow. The discussion concludes with a description of an example computing device architecture, as illustrated in FIG. 11, including example hardware components that can be implemented to perform various computing operations as described herein.

The disclosure now turns to FIG. 1, which illustrates an example eye system 100. The eye system 100 depicts the anatomy of an example eye, which can be treated using the devices, methods, and technologies described herein. The eye system 100 includes an eyeball 102 surrounding an eyelid anatomy including an upper eyelid 130A and a lower eyelid 130B. The eyeball 102 can include a cornea 104, an iris 114, a pupil 108, a lens 110, a vitreous body 112, an anterior chamber 106 between the cornea 104 and the iris 114, a posterior chamber 116 behind the iris 114, a ciliary body 118, a retina 120, a macula 122, a sclera 126 and conjunctiva 128.

The eye system 100 also includes an optic nerve 124 which connects the eyeball 102 to the brain (not shown) and carries electrical impulses from the retina 120 to the brain. Moreover, a central ocular axis 140 of the eyeball 102 can run across the center of the cornea 104, the iris 114, the pupil 108, the lens 110, the vitreous body 112, the anterior chamber 106, and the posterior chamber 116 of the eyeball 102.

FIG. 2A illustrates a bottom view of an example configuration 200 of a speculum 202. The speculum 202 can be used to retract or open the eyelids (e.g., 130A and 130B) of an eye (e.g., 100) during eye surgery. In this example, the speculum 202 includes two arms 204, 206 with blades 210A-B (collectively "210" hereinafter) at the end of each arm. For example, the speculum 202 can include a first arm 204 having a bottom blade 210A and a top blade 210B at its distal end, and a second arm 206 having a bottom blade 210A and a top blade 210B at its distal end. The blades 210 can slip underneath the eyelids (e.g., 130A and 130B) of an eye (e.g., 100) to open, hold, retreat and/or limit movement of the eyelids during surgery. In some examples, an inferior surface 212 of the blades 210 can press against, make contact with, and/or attach to the sclera 126 and/or conjunctiva 128 of the eyeball 102 to open, hold, retreat and/or limit movement of the eyelids (e.g., 130A and 130B) during surgery.

The blades 210 can include apertures 214 for installing, attaching, integrating, securing, and/or implementing light-emitting elements 216 on the blades 210. For example, the bottom blades 210A of the arms 204, 206 can include one or more apertures 214 which can enclose, receive, secure, contain, or retain light-emitting elements 216. The light-emitting elements 216 can include, for example and without limitation, light-emitting diodes (LEDs), fiber optic elements (e.g., fiber optic fibers, filaments, ends, etc.), and the like.

The light-emitting elements 216 can be installed, attached, contained, secured, integrated, placed, and/or implemented into, on, or about the apertures 214 on the blades 210, and can emit light to illuminate and/or transilluminate one or more areas of the eye structure 102, such as the eyelids 130A-B, the cornea 104, the iris 114, the lens 110, the vitreous body 112, the anterior chamber 106, the posterior chamber 116, the ciliary body 118, the retina 120, the macula 122, the sclera 126 the conjunctiva 128, etc. The light from the light-emitting elements 216 can be propagated towards the one or more areas of the eye structure 102 for illumination. In some cases, the surgeon (or any other user or operator) can adjust the direction, target, and/or characteristics of the light (e.g., intensity, brightness, color, etc.) emitted from the light-emitting elements 216 as desired and/or adjust which light-emitting elements 216 to use or activate at any given time.

In some aspects, the light-emitting elements 216 can include a plurality of fiber optic elements (e.g., fiber optic fibers, filaments, ends, etc.), which can provide multiple sources of light, and which can be configured to direct light in the same or different directions, to the same or different targets, and/or with the same or different characteristics such intensity, brightness, color, etc. For example, the light-emitting elements 216 can include multiple fiber optic cables or light-emitting ends on each of the blades. The light and/or the fiber optic cables or light-emitting ends can be adjusted or aimed in different angles, directions, targets, etc., and/or configured to output light with different characteristics, which can be targeted for specific areas of the eye to be illuminated and/or the specific illumination needs or intent for a specific procedure.

For example, the light-emitting elements 216 on each blade 210 can include multiple fiber optic elements configured to emit light in different targeted directions and with different characteristics (e.g., brightness, color, intensity, etc.) tailored for the specific areas of the eye they are intended to illuminate. In one illustrative example, one or more fiber optic elements in the light-emitting elements 216 can be configured to emit brighter light towards a specific area of the eye than other fiber optic elements in the light-emitting elements 216 which may be configured to emit light towards a different area of the eye needing less illumination for a particular procedure or stage in the procedure.

In some examples, the light emitted by the light-emitting elements 216 can be sufficiently powerful to trans-illuminate through multiple layers of the eye, such as the sclera 126, the conjunctiva 128, the retina 120, etc. Moreover, the light emitted by the light-emitting elements 216 can conform to specific standards, such as international standards for endo-illumination, to reduce or eliminate the risk of injury to the eye, such as photochemical damage, thermal damage, light toxicity, etc. The light emitted by the light-emitting elements 216 can provide non-invasive illumination of one or more areas of the eye (e.g., 100), such as the anterior chamber 106, the posterior chamber 116, etc.

The speculum 202 can include a signal carrier 218 that provides light or electricity to the light-emitting elements 216, which the light-emitting elements 216 can use to emit light. The signal carrier 218 can include one or more signal transmission media, such as one or more cables or wires. For example, the signal carrier 218 can include an electrical wire, a fiber optic cable, a set of electrical wires, a set of fiber optic cables, etc. Moreover, the signal carrier 218 can be coupled with, secured or attached to, and/or stabilized on the speculum 202, and configured to run through, along or across the arms 204, 206 of the speculum 202. For example, in some cases, the signal carrier 218 can be secured to the speculum 202 via securing elements 208 on the arms 204, 206, such as clips, ties, or adhesives. In some cases, the securing elements 208 can alternatively or additionally be (or serve as) grips for adjusting or moving the arms 204, 206 (e.g., by squeezing the arms 204, 206) to place the blades 210 on an eye and/or accommodate the eye's size and/or shape.

One end of the signal carrier 218 (e.g., signal carrier end 218A) can connect to a signal source 220, such as a light or power source, which provides signals (e.g., electricity, light) to the signal carrier 218. The signals from the signal source 220 can be transmitted through the signal carrier 218 to the light-emitting elements 216 and used by the light-emitting elements 216 to generate or propagate light.

One or more opposite or other ends of the signal carrier 218 (e.g., signal carrier ends 218B) can run to the apertures 214 on the blades 210 of the speculum 202, and connect to and power the light-emitting elements 216 in the apertures 214, or serve as (or provide) the light-emitting elements 216 in the apertures 214 (e.g., in implementations where the signal carrier 218 is a fiber optic cable and the light-emitting elements 216 are part of the fiber optic cable).

In some examples, the speculum 202 can provide, through the light-emitting elements 216, combined illumination of both the periorbital exterior of the eye (e.g., eyelids 130A and 130B, cornea 104, sclera 126, conjunctiva 128) and the interior of the eye (e.g., iris 114, lens 110, vitreous body 112, retina 120) in a non-invasive (or non-penetrating), trans-corneal, trans-conjunctival and/or trans-scleral manner. Moreover, in some examples, the light-emitting elements 216 can provide non-incandescent, low-temperature light, and, in some cases, at least part of the light-emitting elements can be positioned between the limbus and up to a certain distance, such as 12 mm, posteriorly to achieve retro-illumination.

In some cases, the light-emitting elements 216 and/or the light from the light-emitting elements 216 can be directly placed on the conjunctival tissue (e.g., 128) or transmitted indirectly to the conjunctival tissue surface via the light-emitting elements 216. In some aspects, the light from the light-emitting elements 216 can be sufficiently powerful to trans-illuminate through all the layers of the eye wall (e.g., the conjunctiva 128, sclera 126, retina 120, choroid, etc.).

Figure 2B:
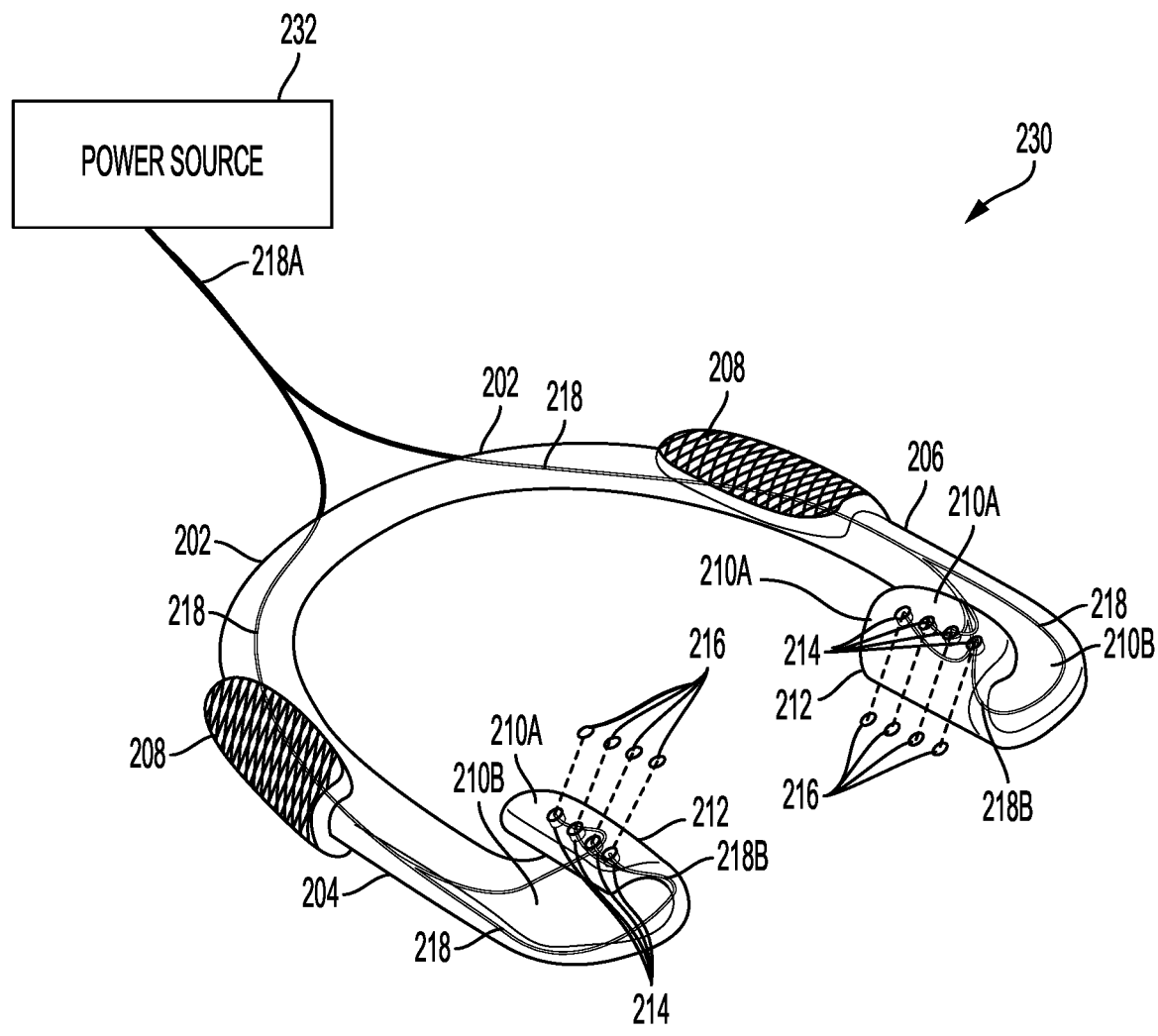

With reference to FIG. 2B, in one example implementation 230 of the speculum 202, the signal carrier 218 can be an electrical wire or cable, the light-emitting elements 216 can be LEDs, and the signal source (220) can be a power source 232. The power source 232 can include, for example and without limitation, one or more batteries, power supplies, power generators, transducers, power adapters, chargers, power stations, electric power systems, etc.

The signal carrier 218 can connect to the power source 232 on one end (e.g., signal carrier end 218A), and the LEDs (i.e., light-emitting elements 216) on opposite or other ends (e.g., signal carrier end 218B). The signal carrier 218 can receive electricity from the power source 232 and transmit the electricity to the LEDs (i.e., light-emitting elements 216). The electricity received by the LEDs (i.e., light-emitting elements 216) through the signal carrier 218 can power the LEDs and allow the LEDs to emit light.

The LEDs (i.e., light-emitting elements 216) can be contained in, inserted into, or positioned on the apertures 216 on the blades 210 of the speculum 202. The LEDs (i.e., light-emitting elements 216) can then receive power from the power source 232 via the signal carrier 218 to generate light and provide illumination for the speculum 202 from their respective locations (e.g., the apertures 216) on the speculum 202.

Figure 2C:
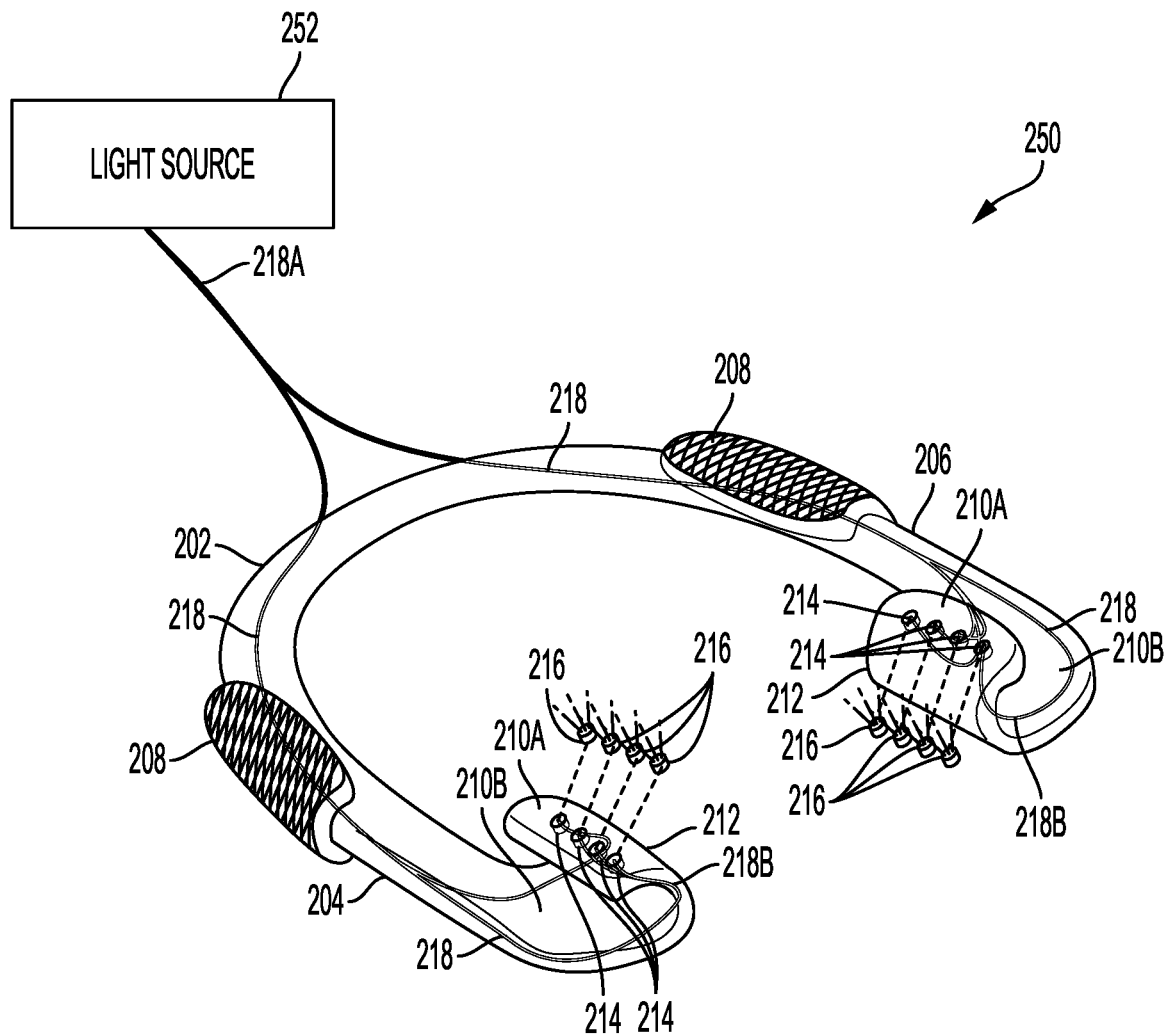

With reference to FIG. 2C, in another example implementation 250 of the speculum 202, the signal carrier 218 can be a fiber optic cable, the signal source 220 can be a light source 252, and the light-emitting elements 216 can be one or more components of the fiber optic cable, such as fiber optic filaments, fibers, strands, illuminators, waveguides, ends, etc. The light source 252 can include any source of light or illumination, such as, for example, an LED, a lamp, a bulb, a laser, a fiber-optic transducer, etc.

The fiber optic cable (i.e., signal carrier 218) can connect to the light source 252 on one end (e.g., signal carrier end 218A) to receive light which is then transmitted through the fiber optic cable and emitted by the fiber optic cable or the light-emitting elements 216 of the fiber optic cable at the opposite or other ends (e.g., signal carrier end 218B) of the fiber optic cable. The fiber optic cable (i.e., signal carrier 218) can run across the arms 204, 206 of the speculum 202 and into or up to the apertures 216, and emit light received from the light source 252 at the ends or termination points (i.e., the light-emitting elements 216) of the fiber optic cable. The fiber optic cable (i.e., signal carrier 218) can be contained in the apertures 216 and provide illumination for the speculum 202 while contained in the apertures 216.

Figure 3A:
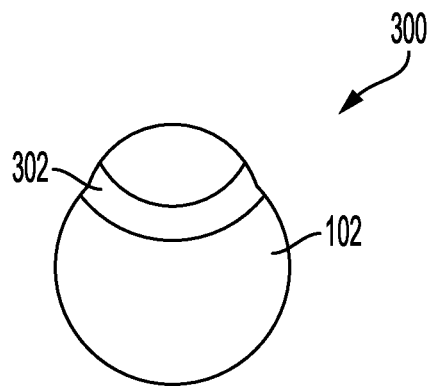
FIG. 3A illustrates an example fitting of an example illumination ring which can be placed on the surface of an eyeball to provide illumination during an eye procedure, in accordance with various embodiments.

FIG. 3A illustrates an example fitting 300 of an example illumination ring-like element 302 which can be placed directly on the surface of the eyeball 102 to provide illumination during an eye procedure. The size and/or characteristics of the ring-like element 302 can be adjustable to accommodate the size and/or shape of the eyeball 102 or customized according to the size and/or shape of the eyeball 102. This can help provide a desired fitting of the ring-like element 302 on the eyeball 102, and ensure the ring-like element 302 remains affixed to the eyeball 102 and/or sufficiently static during a procedure on the eyeball 102. In some cases, the size, shape, and/or properties (e.g., thickness, hardness, etc.) of the ring-like element 302 can prevent illuminated areas of the eye to be blocked by other portions of the eye structure 100, such as the eyelids 130A-B, during a procedure, while allowing the ring-like element 302 to remain affixed to the eyeball 102 and enabling easy and quick removal as desired.

The ring-like element 302 can include light-emitting elements (e.g., 216) for illumination of the eyeball 102 and/or various components of the eye structure (e.g., 100). The number, type, size, positioning, configuration, and/or properties of the light-emitting elements on the ring-like element 302 can vary based on the specific procedure, characteristics of the eyeball 102, illumination needs, eye sensitivities, etc. For example, in some cases, the number, brightness, color, and/or intensity of the light-emitting elements included in the ring-like element 302 can vary according to the size of the eyeball 102, the amount of illumination needed or desired for the specific procedure, the areas that need to be illuminated, etc. Moreover, the light-emitting elements can be positioned at different angles or locations on the ring-like element 302 in different implementations, which can provide different amounts of light and illumination coverage as desired.

In some implementations, the illumination ring-like element 302 can be segmental or non-segmental scleral contour ring-like device for contact stabilization of a light source, such as light-emitting elements (e.g., 216), on an eye (e.g., 102). This illumination ring-like element 302 can direct light in a 360-degree arc through the trans-conjunctival and/or trans-scleral tissue of the eye to provide illumination of the posterior chamber (116), thus providing a red-reflex through the pupil (108) during eye procedures such as cataract surgery. The illumination ring-like element 302

In some cases, the ring-like element 302 can be implemented in combination with speculum 202 to provide additional illumination, coverage, and/or flexibility. For example, the ring-like element 302 can be stabilized on the eyeball (102) and the speculum 202 can be secured on the eyeball (102) and operated together with the ring-like element 302 to provide illumination from both the ring-like element 302 and the speculum 202 (e.g., via the light-emitting elements 216). The ring-like element 302 and/or speculum 202 can be configured to provide illumination to one or more of the same or different areas or angles of the eye.

Moreover, in some cases, the ring-like element 302 and speculum 202 can be configured to provide light with different characteristics. For example, the ring-like element 302 can be configured to provide light with a certain intensity or color tailored for illuminating certain areas of the eye (or the overall eye) while the speculum 202 is configured to provide a different intensity or color tailored for illuminating other areas of the eye (or the overall eye) or tailored for providing a different type or quality of illumination to one or more of the same areas of the eye.

In some cases, the ring-like element 302 can be configured to fit on the eyeball (102) and provide illumination without interfering with the speculum 202. For example, the size, shape, and/or characteristics of the ring-like element 302 can be configured so the ring-like element 302 does not prevent or block the speculum 202 from being attached to the eye or otherwise block light emitted from the speculum 202.

In some implementations, the ring-like element 302 can include one or more apertures on an inner, bottom, or outer surface which can hold one or more sensors to measure various conditions or characteristics of the eye, the ambient light, the light emitted by the ring-like element 302, the environment, etc. For example, one or more sensors can be positioned at one or more locations on the ring-like element 302 to measure brightness, pressure, movement of the ring-like element 302 and/or the eyeball (102), surface conditions (e.g., temperature, air, moisture, etc.), the intensity of the light emitted by the ring-like element 302, the relative differences or similarities between ambient light and the light emitted by the ring-like element 302, moisture or other characteristics of the eyeball (102) which may indicate, for example, irritation, light-sensitivity, or any other conditions.

The sensor measurements can be used to adjust one or more aspects of the ring-like element 302, such as the light intensity, the direction of the light emitted by the ring-like element 302, the number of light-emitting elements activated or used in the ring-like element 302, or any other adjustments that may improve the illumination conditions and coverage while reducing or eliminating unwanted conditions such as eye irritation, photoxicity, or light-sensitivity.

The speculum 202 described herein can similarly be outfitted with one or more sensors to detect various conditions or parameters and make adjustments as desired. In some implementations, the speculum 202 and the ring-like element 302 can be implemented together on the eye as previously described, with one or both being outfitted with one or more sensors to tailor the performance, fitting, configuration, and use of the combined speculum 202 and ring-like element 302 during a procedure.

Figure 3B:
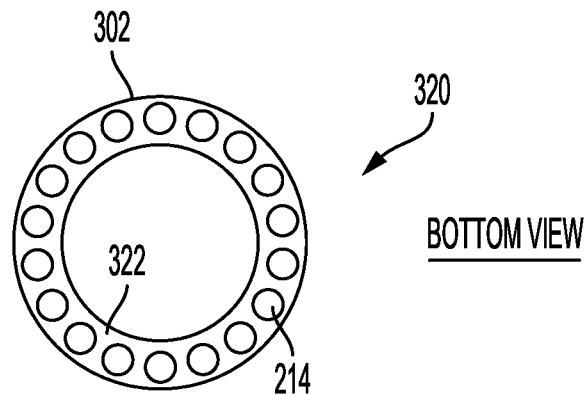
FIG. 3B illustrates a bottom view of the example illumination ring shown in FIG. 3A, in accordance with various embodiments.

FIG. 3B illustrates a bottom view 320 of the example illumination ring-like element 302. Here, a bottom or inner surface 322 of the ring-like element 302 includes a number of light-emitting elements 216. The bottom or inner surface 322 of the ring-like element 302 can be a surface of the ring-like element 302 that faces, or comes in contact with, a surface of the eyeball 102 when the ring-like element 302 is fitted on the eyeball 102 as shown in the example fitting 300 in FIG. 3A, for example.

In some cases, the bottom or inner surface 322 of the ring-like element 302 can be curved, angled or beveled to allow the light-emitting elements 216 to rest flat on the bottom or inner surface 322. In other cases, the bottom or inner surface 322 of the ring-like element 302 can be curved, angled, or beveled in such a way as to allow one or more of the light-emitting elements 216 to rest at a particular angle, which can allow the direction and/or angle of emitted light to be adjusted or customized.

The light-emitting elements 216 can include, for example, LEDs, fiber optics, and/or any other source of light. Moreover, the light-emitting elements 216 can receive power and/or light from an internal and/or external source, as shown in FIG. 3C and further described below.

It should be noted that, while FIG. 3B illustrates the light-emitting elements 216 on the bottom or inner surface 322 of the ring-like element 302, this configuration is provided as a non-limiting example for explanation purposes and other configurations having a different number or placement of the light-emitting elements 216 are possible and contemplated herein. For example, in some cases, a number of light-emitting elements 216 can be placed on a different surface of the ring-like element 302, such as an upper or outer surface, with or without also including a number of light-emitting elements 216 on the bottom or inner surface 322 of the ring-like element 302 as shown in FIG. 3B.

Figure 3C:
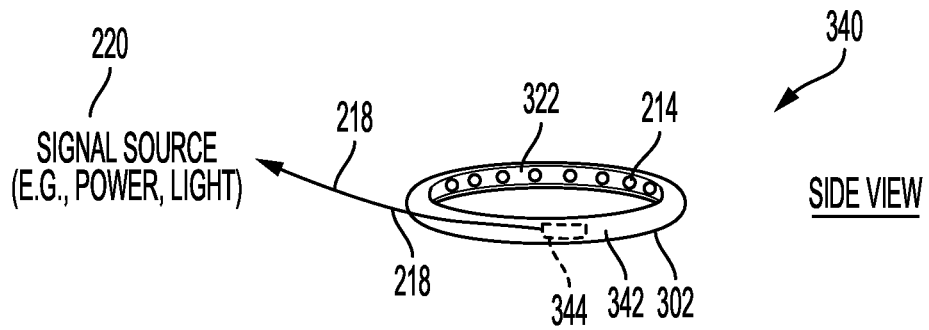
FIG. 3C illustrates a side view of the example illumination ring shown in FIG. 3A, in accordance with various embodiments.

FIG. 3C illustrates a side view 340 of the example illumination ring-like element 302. As illustrated in this example, the light-emitting elements 216 are placed on the bottom or inner surface 322 of the ring-like element 302. In some cases, the light-emitting elements 216 can connect to an external signal source (e.g., 220) via signal carrier 218 to receive light emitted by the light-emitting elements 216 (e.g., if the light-emitting elements 216 are fiber optics) or power used by the light-emitting elements 216 to output light (e.g., if the light-emitting elements 216 are LEDs). Alternatively or additionally, in some cases, the ring-like element 302 can include a battery 344 on or under an outer surface 342 of the ring-like element 302 to power the light-emitting elements 216 and/or any other electrical component in the ring-like element 302. The battery 344 can connect to the light-emitting elements 216 via the signal carrier 218, for example.

Figure 4:
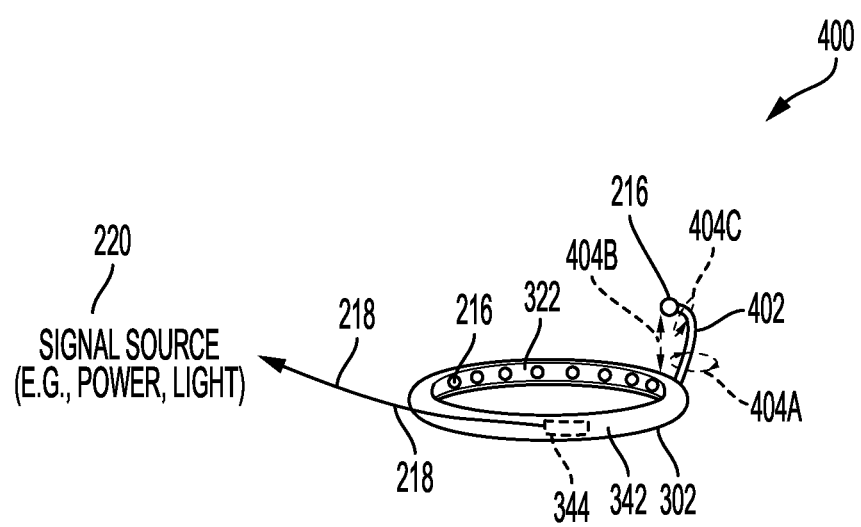
FIG. 4 illustrates an example configuration of an illumination ring where an illumination device is secured on the illumination ring and used to provide additional illumination, in accordance with various embodiments.

FIG. 4 illustrates an example configuration 400 of the illumination ring-like element 302 where an illumination device 402, such as a light (e.g., an LED, a lamp, an optical fiber, etc.), is secured on the ring-like element 302 for additional illumination. The illumination device 402 can be configured to illuminate one or more areas of the eye structure (100), such as, for example, the cornea (104), the iris (114), the pupil (108), the lens (110), the vitreous body (112), the anterior chamber (106), the posterior chamber (116), the ciliary body (118), the retina (120), the macula (122), etc., and the light-emitting elements 216 can be configured to illuminate one or more of the same and/or different areas of the eye structure.

For example, in some cases, the illumination device 402 can be configured to provide retro-illumination of the anterior chamber (106) and/or the posterior chamber (116) of the eyeball (102), and/or direct or indirect transcorneal or paralimbal illumination of the anterior chamber (106) of the eyeball (102). The illumination device 402 can be aimed, focused, directed, etc., in a specific way to provide retro-illumination of the anterior chamber (106) and/or the posterior chamber (116) of the eyeball (102), and/or direct or indirect transcorneal or paralimbal illumination of the anterior chamber (106) of the eyeball (102). Moreover, the light-emitting elements 216 on the surface 322 of the ring-like element 302 can be configured to illuminate the posterior chamber (116) and provide a red-reflex through the pupil (108). In some cases, the light-emitting elements 216 on the surface 322 of the ring-like element 302 can also be configured to provide additional illumination to areas illuminated by the illumination device 402, such as the anterior segment (106), or illuminate other areas of the eye structure (100).

The illumination device 402 can include a light-emitting element 216, such as an LED or fiber optic end, that emits light for illumination. Moreover, the illumination device 402 can be adjustable along one or more axes 404A-C to change the direction of emitted light, the areas of illumination from the emitted light, the height of the illumination device 402 or its vertical distance from a point of reference such as a surface of the ring 102 (e.g., 322, 342) or a surface of the eyeball (102), the azimuth of the illumination device 402. For example, the illumination device 402 can be moved or rotated along a longitudinal axis (e.g., roll), a vertical axis (e.g., yaw) and a transverse or lateral axis (e.g., pitch).

In the example configuration 400, the light-emitting elements 216 and/or the illumination device 402 can connect to an external signal source (e.g., 220) via signal carrier 218 to receive light emitted by the light-emitting elements 216 (e.g., if the light-emitting elements 216 are fiber optics) or power used by the light-emitting elements 216 to output light (e.g., if the light-emitting elements 216 are LEDs). Alternatively or additionally, in some cases, the ring-like element 302 can include a battery 344 on or under the outer surface 342 of the ring-like element 302 to power the light-emitting elements 216 and/or the illumination device 402. The battery 344 can connect to the light-emitting elements 216 via the signal carrier 218, for example.

Figure 5:
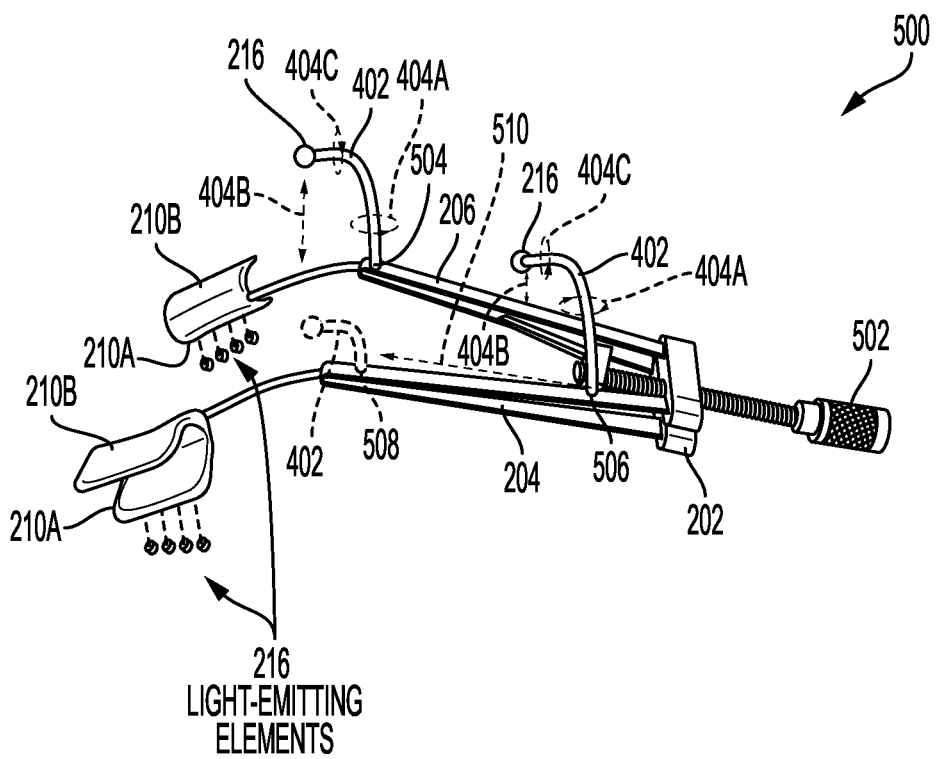
FIG. 5 illustrates an example configuration of a speculum with multiple illumination devices and light-emitting elements, in accordance with various embodiments.

FIG. 5 illustrates an example configuration 500 of a speculum 202 with multiple illumination devices 402 and light-emitting elements 216. In this example, the speculum 202 includes an illumination device 402 at a first location 504 on arm 206 of the speculum 202, and an illumination device 402 at a second location 506 on arm 204 of the speculum 202. The speculum 202 also includes light-emitting elements 216 on the blades 210 of the speculum 202. In this example, the light-emitting elements 216 are located on the bottom blades 210A of the speculum 202.

The illumination devices 402 on the arms 204, 206 can be adjusted along one or more axes (404A, 404B, 404C), as previously described. Moreover, in some cases, the illumination devices 402 can be moved 510 from one location to another. For example, the illumination device 402 in location 506 on the arm 204 can be moved 510 to a different location 508 on the arm 204. The illumination device 402 can be moved using any position adjustment mechanism, such as a detach/unsecure and attach/secure mechanism that allows the illumination device 402 to be detached/unsecured from one location and attached/secured to another location, a sliding mechanism that allows the illumination device 402 to slide to a different position on the arm 204, etc.

The illumination devices 402 on the arms 204, 206 of the speculum 202 and the light-emitting elements 216 on the blades 210 of the speculum 202 can be configured to illuminate one or more areas of the eye structure (100), such as, for example, the cornea (104), the iris (114), the pupil (108), the lens (110), the vitreous body (112), the anterior chamber (106), the posterior chamber (116), the ciliary body (118), the retina (120), the macula (122), etc., and the light-emitting elements 216 can be configured to illuminate one or more of the same and/or different areas of the eye structure. The illumination devices 402 on the arms 204, 206 of the speculum 202 and the light-emitting elements 216 on the blades 210 of the speculum 202 can illuminate one or more of the same areas or one or more different areas.

For example, in some cases, the illumination devices 402 on the arms 204, 206 of the speculum 202 can be configured to provide retro-illumination of the anterior chamber (106) and/or the posterior chamber (116), and/or direct or indirect transcorneal or paralimbal illumination of the anterior chamber (106), while the light-emitting elements 216 can be configured to illuminate the posterior chamber (116) and provide a red-reflex through the pupil (108). In some cases, the light-emitting elements 216 on the blades 210 can also be configured to provide additional illumination to areas illuminated by the illumination devices 402, such as the anterior segment (106), or illuminate other areas of the eye structure (100).

In some implementations, the light-emitting elements 216 on the blades 210 can function as conjunctival surface lights, and the illumination devices 402 on the arms 204, 206 can function as adjustable anterior segment lights. Moreover, in some implementations, the configuration 500 of the speculum 202 can include more or less illumination devices 402 than those shown in FIG. 5. For example, the speculum 202 can include one or more additional illumination devices positioned at one or more different locations of the speculum 202.

The illumination devices 402 on the arms 204, 206 of the speculum 202 and the light-emitting elements 216 on the blades 210 of the speculum 202 can receive power and/or light from a signal source (e.g., 220) through a signal carrier (e.g., 218), as previously described. Moreover, the speculum 202 in configuration 500 can include an adjustment element 502 that can be used to adjust the positioning of the arms 204, 206 and blades 210 of the speculum 202. For example, the adjustment element 502 can be used to further open or close the arms 204, 206 and thus increase or decrease the distance between the arms 204, 206 and blades 210 to a level that suits a particular eye structure.

Figure 6:
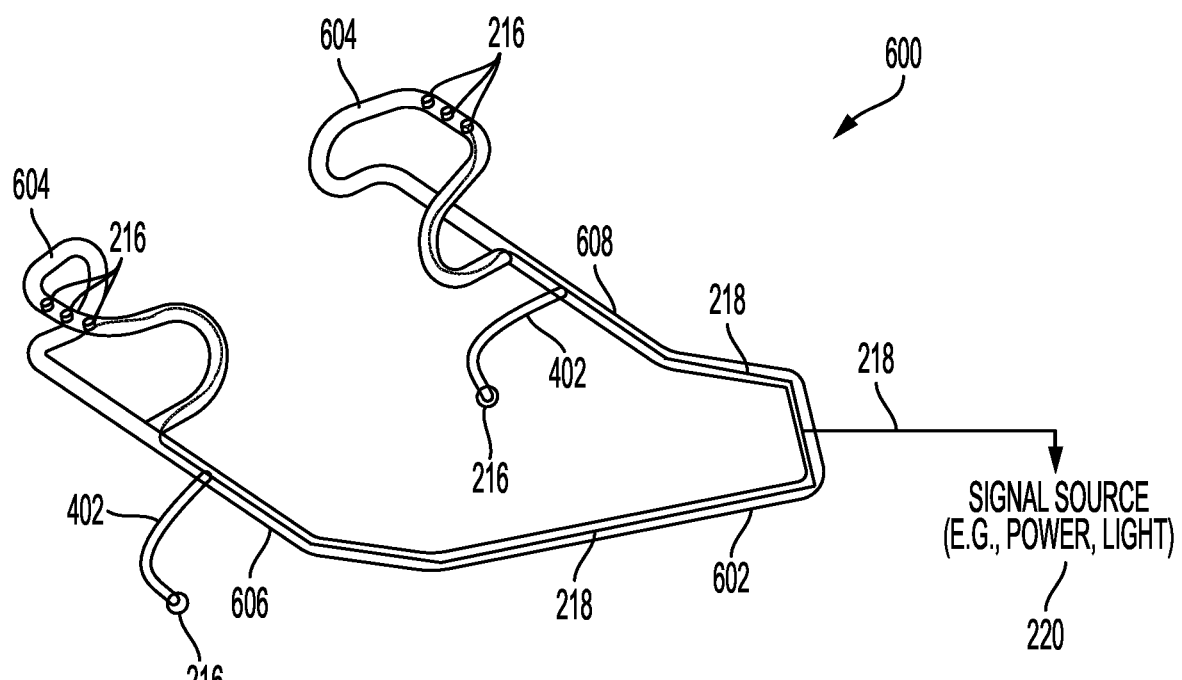
FIG. 6 illustrates an example configuration of a wire speculum, in accordance with various embodiments.

FIG. 6 illustrates an example configuration 600 of a wire speculum 602. The wire speculum 602 can include wire arms 606, 608 and wire blades 604. Each wire arm can include a wire blade. For example, wire arm 606 can include a wire blade 604 and wire arm 608 can also include a wire blade 604. In some implementations, the wire speculum 602 can implement Kirschner wires (K-wires). For example, the wire arms 606, 608 can be K-wire arms and the wire blades 604 can be K-wire blades.

Each of the wire blades 604 can include one or more light-emitting elements 216. The wire arms 606, 608 can include a signal carrier 218 that connects to a signal source 220 and either connects to the light-emitting elements 216 on the wire blades 604 or includes/provides the light-emitting elements 216 on the wire blades 604. In one example, the light-emitting elements 216 can be electrical light sources that are separate from the signal carrier 218, such as separate LEDs, and the signal carrier 218 can connect to the light-emitting elements 216 on the wire blades 604 to provide the light-emitting elements 216 power obtained from the signal source 220.

In another example, the signal carrier 218 can include a fiber optic cable and the light-emitting elements 216 can be part of the fiber optic cable (e.g., fiber optic strands, filaments, ends, points, etc.). The fiber optic cable can connect to a light source (e.g., signal source 220) to receive light and transmit the light across the fiber optic cable to be emitted as light at the end of the fiber optic cable (e.g., the light-emitting elements 216).

In some cases, the wire speculum 602 can also include one or more illumination devices 402 installed on one or more of the arms 606, 608 of the wire speculum 602. The one or more illumination devices 402 can be adjustable as previously described. Moreover, the number and/or location of illumination devices (402) on the wire speculum 602 can vary in different implementations.

Figure 7:
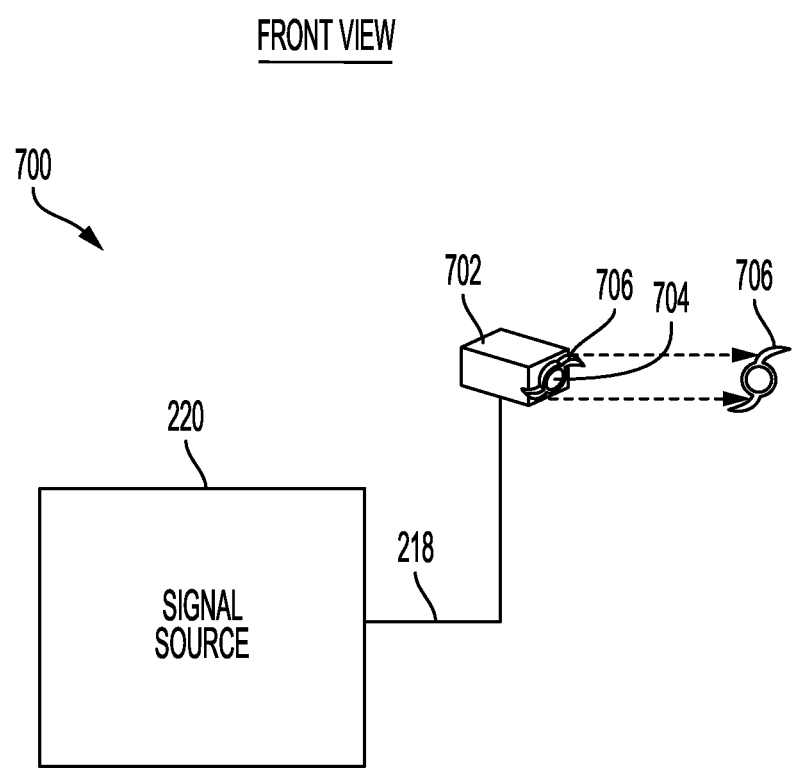
FIG. 7 illustrates a front view of an example standalone light head that can attach to one or more areas of the eye using one or more attaching elements, in accordance with various embodiments.

FIG. 7 illustrates a front view 700 of an example standalone light head 702 that can attach to the conjunctiva 128 using one or more attaching elements 706 that can secure or fasten the standalone light head 702 to the conjunctiva 128 and sclera 126. In some implementations, the attaching elements 706 can be rotational barbs that can secure or fasten the standalone light head 702 to the surface of the conjunctiva 128 and sclera 126 while allowing quick removal without the use of additional attachment devices such as sutures or glue.

The standalone light head 702 can include a light output port 704 that emits light for illumination. The light output port 704 can be, for example, an LED or a portion of a fiber optic cable (e.g., fiber optic filament, fiber, strand, end, etc.). The standalone light head 702 can include a signal carrier 218, such as an electrical wire or a fiber optic cable, that connects to a signal source 220 to receive power or light for the light output port 704. The signal carrier 218 can transmit power or light from the signal source 220 to the light output port 704, which can then use the power or light to emit light.

Figure 8:
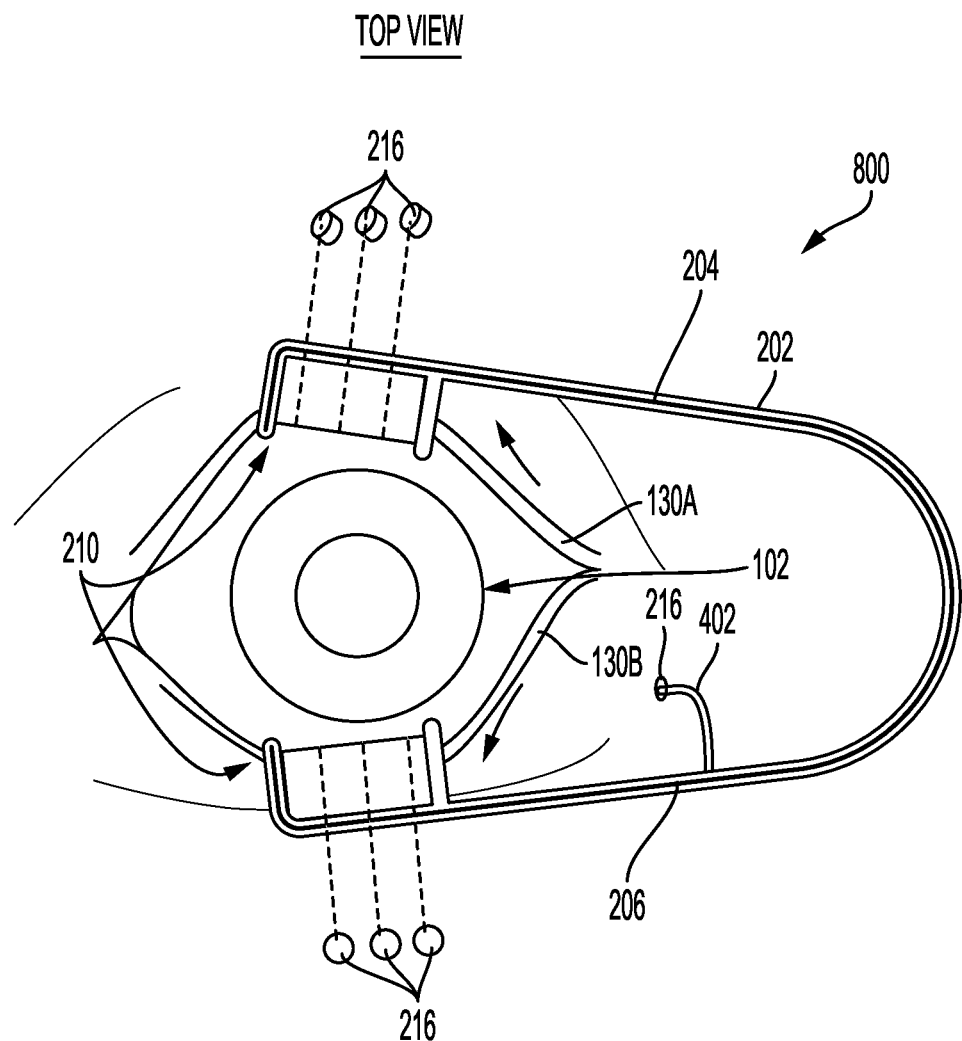
FIG. 8 illustrates an example placement of a speculum on an eye system for access and illumination of one or more areas of the eye system, in accordance with various embodiments.

FIG. 8 illustrates an example placement 800 of a speculum 202 on an eye system for access and illumination of one or more areas of the eye system. In this example, the blades 210 of the speculum can slip underneath the eyelids 130A and 130B of an eye system (e.g., 100) to open, hold, retreat and/or limit movement of the eyelids 130A and 130B during surgery or any other eye procedure. In some examples, a surface of the blades 210, such as an inferior surface of the blades 210, can press against, make contact with, and/or attach to the sclera (126) and/or conjunctiva (128) of the eyeball 102 to open, hold, retreat and/or limit movement of the eyelids 130A and 130B and provide access to the eyeball 102.

The speculum 202 includes light-emitting elements 216 on the blades 210 to provide illumination of one or more areas of the eyeball 102. In some implementations, the speculum 202 can also include one or more illumination devices 402 to provide additional illumination to one or more areas of the eyeball 102.

The light-emitting elements 216 on the blades 210 and/or the one or more illumination devices 402 on the speculum 202 can provide combined illumination of both the periorbital exterior of the eyeball 102 (e.g., the eyelids 130A-130B, the cornea 104, the sclera 126, the conjunctiva 128, etc.) and the interior of the eyeball 102 (e.g., the iris 114, the lens 110, the vitreous body 112, the retina 120, etc.). Moreover, the light-emitting elements 216 on the blades 210 and/or the one or more illumination devices 402 on the speculum 202 can use non-invasive (or non-penetrating), trans-corneal, trans-conjunctival and/or trans-scleral, non-incandescent, low-temperature light, which in some examples can be at least partly positioned between the limbus (e.g., the junction of the cornea 104 and sclera 126) and up to a distance, such as 12 mm, posteriorly to achieve retro-illumination.

In some cases, the light-emitting elements 216 and/or light from the light-emitting elements 216 can be directly placed on the conjunctival tissue. In other cases, the light from the light-emitting elements 216 can be transmitted indirectly to the conjunctival tissue surface via, for example, optical fiber. The light from the light-emitting elements 216 and/or the one or more illumination devices 402 can be sufficiently powerful to trans-illuminate through layers of the eyeball 102, such as the sclera 126, the conjunctiva 128, the retina 120, etc.).

Figure 9:
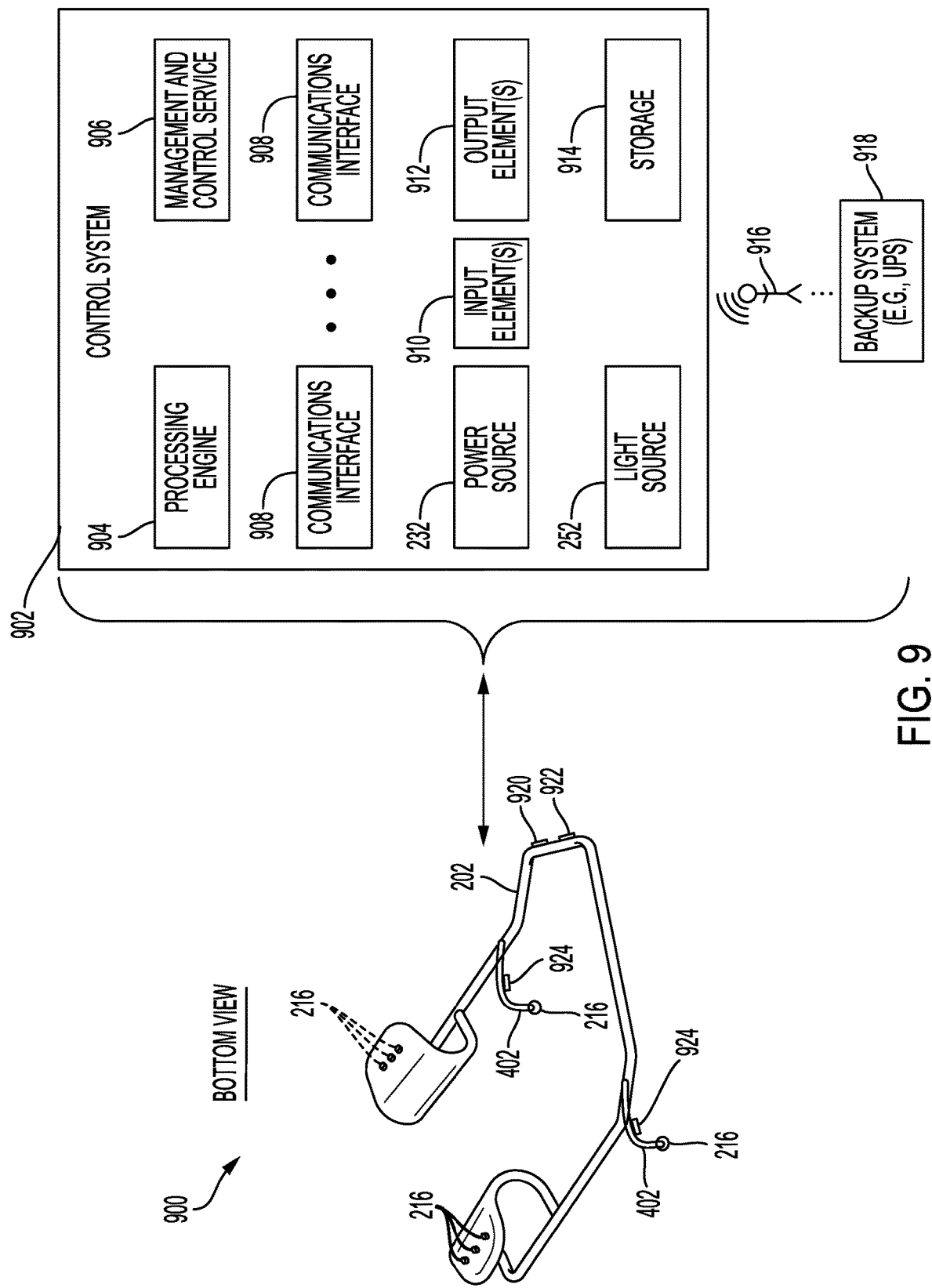
FIG. 9 illustrates a diagram of an example use scenario for interacting with an example speculum, in accordance with various embodiments.

FIG. 9 illustrates a diagram 900 of an example use scenario for interacting with the speculum 202. In this example, a control system 902 can communicate with the speculum 202 to control, monitor, manage, use, and/or adjust a usage or operation of the speculum 202, collect data from the speculum 202, provide data to the speculum 202, and/or otherwise interact with the speculum 202.

The speculum 202 can include a communications interface 920, such as a wired or wireless communications interface, to transmit and receive data from other devices such as the control system 902. The speculum 202 can also include a processing element 922, such as a processor device, which can receive information from the communications interface 920, such as instructions or parameters provided by the control system 902, and perform operations or functions to control components of the speculum 202, such as the light-emitting elements 216 and/or the one or more illumination devices 402, generate data such as notifications or statistics for the control system 902, etc.

The control system 102 can include one or more computing devices, such as a server, a laptop computer, a desktop computer, a tablet computer, a smartphone, a smart device, a computer station, etc. Moreover, the control system 102 can include a processing engine 904 for processing data, performing computer operations and functions, generating data and outputs, performing calculations, generating instructions, etc. For example, the processing engine 904 can control the function and operation of the control system 102; monitor and/or control the operation of the speculum 202; generate data (e.g., instructions, outputs, etc.) for the speculum 202, a human operator 916, and/or other devices; processing data from the speculum 202, the human operator 916, and/or other devices; perform calculations and determinations, such as artificial intelligence or machine learning functions; etc.

In some examples, the processing engine 904 can perform speech recognition to process speech information, such as speech commands, from the human operator 916; gesture recognition to process and recognize gestures from the human operator 916, such as gesture commands; detection or recognition operations to detect and recognize objects (e.g., tissue, areas of the eye, medical instruments, etc.), light or characteristics of light, patterns, etc.; machine learning; etc. For example, the processing engine 904 can receive images collected by a camera 924 on the speculum 202 which depict features of the eye, characteristics of the illumination of the eye, etc., and use machine learning to detect or recognize patterns, features of the eye in the images, illumination characteristics captured in the images, etc.; and generate data such as instructions, recommendations, or parameters based on the detected or recognized information. To illustrate, the processing engine 904 can process images and generate outputs for controlling the amount, direction, or intensity of light emitted by the light-emitting elements 216 and/or the illumination devices 402, adjust the operations of the speculum 202, generate recommendations for the human operator 916, etc.

The control system 902 can include a management and control service 906 which performs management and control functions in coordination with the processing engine 904. The management and control functions can include management and control operations for the control system 902 and/or the speculum 202, such as adjusting operating parameters, scheduling functions, monitoring operations and conditions at the control system 902 and/or the speculum 202, etc.

The control system 902 can include one or more communications interfaces 908 for communicating data with other devices, such as the speculum 202. The one or more communications interfaces 908 can include a physical connection interface, such as an Ethernet cable or fiber optic interface, and/or a wireless interface such as a WiFi interface, a Bluetooth interface, a radio antenna, etc.

The control system 902 can include a power source 232, such as a battery or power supply, and a light source 252, such as a fiber-optic transducer or a lamp. In some cases, the power source 232 and/or the light source 252 can connect to the speculum 202 via a signal carrier (e.g., 218), such as a fiber optic cable or an electrical wire, to provide power and/or light to components of the speculum 202, such as the light-emitting elements 216, the illumination devices 402, the communications interface 920, the processing element 922, the camera 924, etc.

The control system 902 can include one or more input elements 910, such as a microphone, a camera, a keyboard, a touchscreen, a sensor, etc. The one or more input elements 910 can be used by the human operator 916 to interact with the control system 902. For example, the one or more input elements 910 can be used by the human operator 916 to provide speech or gesture commands to the control system 902, access information or functions on the control system 902, input commands or information into the control system 902, etc.

The control system 902 can also include one or more output elements 912, such as one or more video, audio, and/or text output devices (e.g., a speaker, a display, an interface, etc.).

The control system 902 can include a storage 914, such as one or more storage drives, memories, caches, etc. The storage 914 can store instructions, data, software, logs, files, etc.

Through the control system 902, the human operator 916 can interact with the speculum 202 to monitor, manage, and/or modify operations of the various components of the speculum 202 (e.g., the light-emitting elements 216, the illumination devices 402, the communications interface 920, the processing element 922, the camera 924, etc.), and can provide and access information such as instructions, notifications, usage information, input data, recommendations, reports, operation parameters, etc.

In some cases, a backup system 918 can be provided for backup power or processing. For example, an uninterruptible power supply (UPS) system (e.g., 918) can be provided for backup power to the control system 902 and/or the speculum 202 in case of a failure or error by one or more power sources, such as power source 232, a battery on the speculum 202, a power supply connected to a signal carrier (e.g., 218) on the speculum 202, etc. The backup system 918 can provide redundancy and fault tolerance to avoid system failures during a procedure that could affect the functioning or operation of the speculum 202 and/or the safety of a patient.

Figure 10:
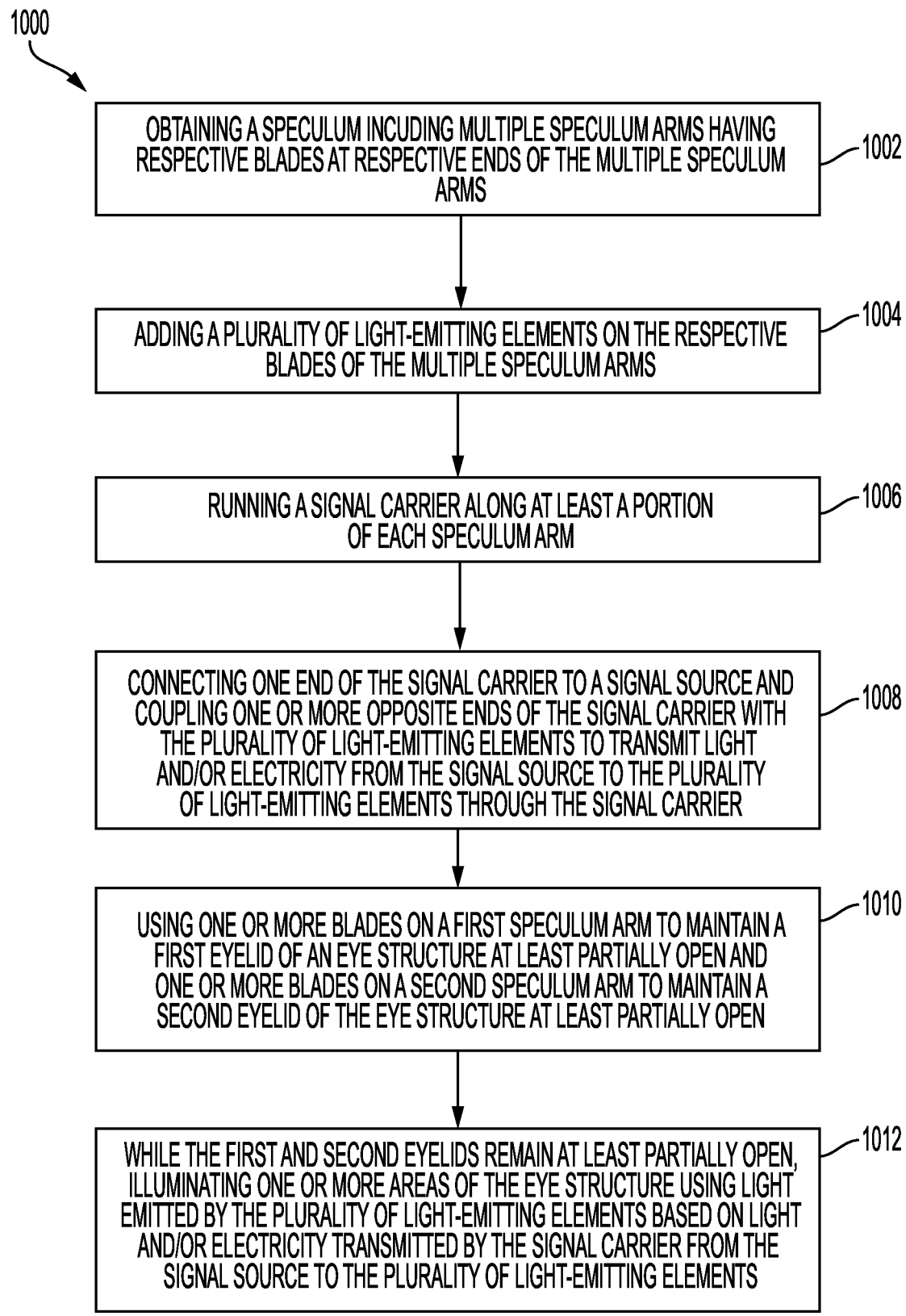
FIG. 10 illustrates an example method for providing illumination of the periorbital exterior of the eye and the interior of the eye with a non-invasive (or non-penetrating), trans-corneal, trans-conjunctival, trans-scleral, non-incandescent, and/or low-temperature light source, in accordance with various embodiments.
Figure 11:
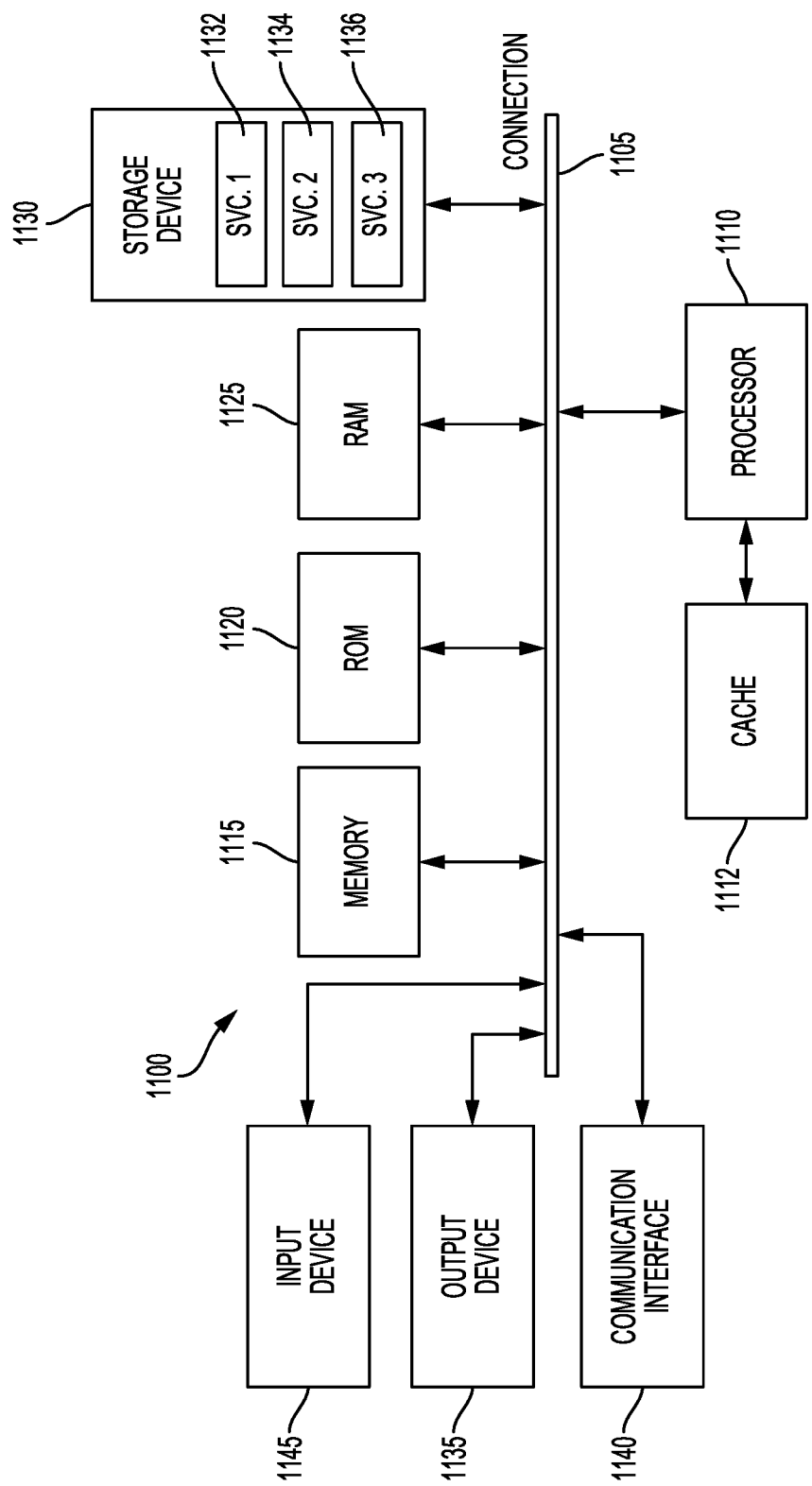
FIG. 11 illustrates an example computer system architecture of a computing device which can be used to implement computing operations in accordance with various embodiments.

Having disclosed example system components and concepts, the disclosure now turns to the example method 1000 for providing illumination of the periorbital exterior of the eye and the interior of the eye with a non-invasive (or non-penetrating), trans-corneal, trans-conjunctival, trans-scleral, non-incandescent, and/or low-temperature light source, as shown in FIG. 10. For the sake of clarity, the method 1000 is described with reference to the eye structure 100 and the speculum 202, as variously shown in FIGS. 1-2C and 5-9. The steps outlined herein are examples and can be implemented in any combination thereof, including combinations that exclude, add, or modify certain steps.

At step 1002, the method can include obtaining a speculum 202 including speculum arms (204 and 206) having respective blades (210) at respective ends of the speculum arms (204 and 206). In some cases, the speculum can include two arms (204 and 206) and the respective blades (210) can include a bottom blade (210A) and a top blade (210B) at each speculum arm. The blades (210) can also include apertures (214) or openings for receiving, retaining, and/or containing light-emitting elements (216).

At step 1004, the method can include adding a plurality of light-emitting elements (216) on the respective blades (210) of the speculum arms (204 and 206). The light-emitting elements (216) can be inserted into, retained by, and/or contained or enclosed at least partially within apertures (214) or openings on the blades (210). In some cases, the light-emitting elements (216) can include LEDs configured to emit light from their locations on the blades (210). In other examples, the light-emitting elements (216) can include fiber optic cables or elements, such as fiber strands, fiber filaments, fibers, fiber cable ends or output points, etc.

At step 1006, the method can include running a signal carrier (218) along at least a portion of each speculum arm (204 and 206). The signal carrier (218) can be attached, secured, fastened, coupled, clipped, retained, stabilized, or otherwise positioned on at least a portion of each speculum arm (204 and 206) to run along each arm toward the blades (210) on the speculum arms and the light-emitting elements (216) on the blades (210). The signal carrier (218) can include, for example, an electrical wire capable of transmitting or carrying electricity to the light-emitting elements (216), or a fiber optic cable capable of transmitting or carrying light to the light-emitting elements (216).

At step 1008, the method can include connecting one end (218A) of the signal carrier (218) to a signal source (220) and coupling one or more opposite ends (218B) of the signal carrier (218) with the plurality of light-emitting elements (216), to transmit light and/or electricity from the signal source (220) to the plurality of light-emitting elements (216) through the signal carrier (218). For example, if the light-emitting elements (216) include LEDs, the signal carrier (218) can connect to the signal source (220) to receive and transmit electricity to the LEDs for powering the LEDs and enabling the LEDs to emit light. As another example, if the light-emitting elements (216) include fiber optic cable elements, the signal carrier (218) can be a fiber optic cable which connects to the signal source (220) to receive and transmit light to the light-emitting elements (216) to be emitted by the light-emitting elements (216) for illumination.

At step 1010, the method can include using one or more blades (210) on a first speculum arm (e.g., 204) to maintain a first eyelid (e.g., 130A) of an eye structure (e.g., 100) at least partially open and one or more blades (210) on a second speculum arm (e.g., 206) to maintain a second eyelid (e.g., 130B) of the eye structure (e.g., 100) at least partially open. In some cases, the one or more blades (210) on the first and speculum arms (204 and 206) can be placed underneath the eyelids (130A and 130B) of the eye structure (100) to open, hold, or limit a movement of the eyelids (130A and 130B) during an eye procedure. In some examples, an inferior surface (e.g., 212) of the blades (210) on the first and/or second speculum arms can make contact with or attach to a sclera (e.g., 126) or conjunctiva (e.g., 128) of an eyeball (e.g., 102) associated with the eye structure (100) in order to open, hold, or limit movement of the eyelids (130A and 130B) during an eye procedure.

At step 1012, while the eyelids (130A and 130B) remain at least partially open, the method can include illuminating one or more areas of the eye structure (100) using light emitted by the plurality of light-emitting elements (216) based on light and/or electricity transmitted by the signal carrier (218) from the signal source (220) to the plurality of light-emitting elements (216). In one example, the light-emitting elements (216) can include LEDs which emit light for illumination based on electricity received by the LEDs from the signal source (220) through the signal carrier (218). The signal carrier (218) here can be a wire connected to the signal source (220) and the LEDs, that transmits electricity from the signal source (220) to the LEDs.

In another example, the light-emitting elements (216) include fiber optic cable elements which emit light for illumination based on light provided by the signal carrier (218) from the signal source (220). Here, the signal carrier (218) can be a fiber optic cable connected to the signal source (220) on one end and coupled with (or including) the light-emitting elements 216 on other ends of the fiber optic cable. The fiber optic cable (e.g., the signal carrier) can transmit light to the light-emitting elements 216, which can be part of the fiber optic cable (e.g., fiber strands, filaments, ends, output points, fibers, etc.) or separate components (e.g., interfaces, ports, fiber optic cables or elements, etc.) capable of receiving and emitting light from the fiber optic cable.

In some implementations, the speculum 202 can include one or more adjustable illumination devices (e.g., 402) positioned at one or more respective locations on the speculum 202. The illumination devices can be, for example, lights or light devices that can be secured, fastened, attached, coupled, integrated, etc., with the speculum 202 at one or more locations on the speculum 202. In some examples, the illumination devices (402) can be anterior segment lights containing a light-emitting element, such an LED or fiber optic cable element, configured to illuminate one or more areas of the eye, such as an anterior chamber (106).

The one or more adjustable illumination devices (e.g., 402) can be coupled with (or connected to) the signal carrier (218), which can provide light (e.g., if the one or more adjustable illumination devices use or include fiber optics) and/or electricity (e.g., if the one or more adjustable illumination devices use or include LEDs or other electrical light devices) to the one or more adjustable illumination devices (e.g., 402). The light and/or electricity received from the signal carrier (218) can allow the one or more adjustable illumination devices (e.g., 402) to emit light and provide additional illumination to the eye structure (100).

The light-emitting elements (216) and/or the one or more adjustable illumination devices (402) on the speculum 202 can provide combined illumination of both the periorbital exterior of the eye (e.g., the eyelids 130A-B, the cornea 104, the sclear 126, the conjunctiva 128, etc.) and the interior of the eye (e.g., the iris 108, the lens 110, the vitreous body 112, the retina 120, etc.), using non-invasive (or non-penetrating), trans-corneal, trans-conjunctival and/or trans-scleral, non-incandescent, low-temperature light.

In some implementations, the method can include placing or securing a ring structure (302) on an eyeball (102) to provide illumination of one or more areas of the eyeball (102). The right structure (302) can fit on the eyeball (102) and can include light-emitting elements (216) on an inner surface of the ring structure (302) and a signal carrier (318) for providing light and/or electricity to the light-emitting elements (216). In some cases, the ring structure (302) can also include one or more adjustable illumination devices (402) at one or more locations on an outer surface of the ring structure (302), which can provide additional illumination to one or more of the same or different areas of the eyeball (102). The one or more adjustable illumination devices (402)

can receive light from the signal carrier (318) and/or electricity from the signal carrier (318) and/or a battery (344) on the ring structure (302).

In other implementations, the method can include attaching a standalone light head (e.g., 702) to the eyeball (102) using one or more attaching elements (e.g., 706) that can secure, attach, and/or fasten the standalone light head (702) to one or more areas of the eyeball (102). For example, the one or more attaching elements can include rotational barbs that can attach to a surface of the sclera (126) and/or the conjunctiva (128), and which allow quick removal without the use of additional attachment devices such as sutures or glue.

The standalone light head (702) can include a light output port (704) that emits light for illumination. The light output port (704) can be, for example, an LED or a portion of a fiber optic cable (e.g., fiber optic filament, fiber, strand, end, etc.). The standalone light head (702) can include a signal carrier (218), such as an electrical wire or a fiber optic cable, that connects to a signal source (220) to receive power or light for the light output port (704). The signal carrier (218) can transmit power or light from the signal source (220) to the light output port (704), which can then use the power or light to emit light.

The disclosure now turns to FIG. 11, which illustrates an example computing system architecture 1100 including various hardware components which can be implemented with a speculum 202 and/or a computing device, such as a control system 102, and which can be configured to perform various computing operations as described herein.

In this example, the computing system architecture 1100 includes components in electrical communication with each other using a connection 1105, such as a bus. The computing system architecture 1100 includes a processing unit (CPU or processor) 1110 and a system connection 1105 that couples various system components including the system memory 1115, such as read only memory (ROM) 1120 and random access memory (RAM) 1125, to the processor 1110. The computing system architecture 1100 can include a cache of high-speed memory connected directly with, in close proximity to, or integrated as part of the processor 1110. The computing system architecture 1100 can copy data from the memory 1115 and/or the storage device 1130 to the cache 1112 for quick access by the processor 1110. In this way, the cache can provide a performance boost that avoids processor 1110 delays while waiting for data. These and other modules can control or be configured to control the processor 1110 to perform various actions. Other system memory 1115 may be available for use as well. The memory 1115 can include multiple different types of memory with different performance characteristics. The processor 1110 can include any general purpose processor and a hardware or software service, such as service 1 1132, service 2 1134, and service 3 1136 stored in storage device 1130, configured to control the processor 1110 as well as a special-purpose processor where software instructions are incorporated into the actual processor design. The processor 1110 may be a completely self-contained computing system, containing multiple cores or processors, a bus, memory controller, cache, etc. A multi-core processor may be symmetric or asymmetric.

To enable user interaction with the computing system architecture 1100, an input device 1145 can represent any number of input mechanisms, such as a microphone for speech, a touch-sensitive screen for gesture or graphical input, keyboard, mouse, motion input, speech and so forth. An output device 1135 can also be one or more of a number of output mechanisms known to those of skill in the art. In some instances, multimodal systems can enable a user to provide multiple types of input to communicate with a computing device configured according to the computing system architecture 1100. The communications interface 1140 can generally govern and manage the user input and system output. There is no restriction on operating on any particular hardware arrangement and therefore the basic features here may easily be substituted for improved hardware or firmware arrangements as they are developed.

Storage device 1130 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1125, read only memory (ROM) 1120, and hybrids thereof.

The storage device 1130 can include services 1132, 1134, 1136 for controlling the processor 1110. Other hardware or software modules are contemplated. The storage device 1130 can be connected to the system connection 1105. In one aspect, a hardware module that performs a particular function can include the software component stored in a computer-readable medium in connection with the necessary hardware components, such as the processor 1110, connection 1105, output device 1135, and so forth, to carry out the function.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" refers to at least one of a set and indicates that one member of the set or multiple members of the set satisfy the claim. For example, claim language reciting "at least one of A and B" means A, B, or A and B.

What is claimed is:

1. An apparatus comprising:
   a ring structure configured to sit on a surface area of an eye;
   a plurality of light-emitting elements;
   a plurality of apertures on the ring structure configured to receive the plurality of light-emitting elements, the plurality of light-emitting elements being configured to provide illumination to one or more areas of the eye from a location at least partially within the plurality of apertures;
   a signal carrier running along at least a portion of the ring structure, the signal carrier having one end configured to connect to a signal source and receive at least one of light and electricity from the signal source, and one or more opposite ends respectively coupled with the plurality of light-emitting elements, the signal carrier being configured to transmit the at least one of the light and electricity from the signal source to the plurality of light-emitting elements; and
   one or more adjustable anterior segment lights positioned at one or more respective locations on an outer surface of the ring structure, the one or more adjustable anterior segment lights being coupled with the signal carrier, the signal carrier providing at least one of light and electricity used by the one or more adjustable anterior segment lights to provide additional illumination to the eye.

2. The apparatus of claim 1, wherein the plurality of light-emitting elements are positioned on a curved or concave inner surface of the ring structure with each respective light-emitting end of the plurality of light-emitting elements facing away from the curved or concave inner surface of the ring structure.

3. The apparatus of claim 1, wherein the signal carrier comprises an electrical cable, wherein the signal source comprises a power source, and wherein the plurality of light-emitting elements comprises light-emitting diodes (LEDs).

4. The apparatus of claim 1, wherein the signal carrier comprises a fiber optic cable, wherein the signal source comprises a light source, and wherein the plurality of light-emitting elements comprises respective portions of the fiber optic cable.

5. The apparatus of claim 4, wherein the respective portions of the fiber optic cable comprise at least one of fiber strands, fiber filaments, fibers, and fiber cable ends.

6. The apparatus of claim 1, wherein the signal source comprises at least one of a battery and a power supply.

7. The apparatus of claim 1, wherein the plurality of apertures on the ring structure are configured such that the plurality of apertures are equally positioned along an entire length of the ring structure.

8. The apparatus of claim 1, further comprising:
   an illumination device extending from the ring structure to provide additional illumination.

9. The apparatus of claim 8, wherein the illumination device comprises a light-emitting diode (LED).

10. The apparatus of claim 8, wherein the illumination device is adjustable by a user to position the illumination device in a chosen direction.

11. The apparatus of claim 10, wherein the non-transitory signal carrier comprises a fiber optic cable, wherein the signal source comprises a light source, and wherein the plurality of light-emitting elements comprises respective portions of the fiber optic cable.

12. The apparatus of claim 11, wherein the respective portions of the fiber optic cable comprise at least one of fiber strands, fiber filaments, fibers, and fiber cable ends.

13. An apparatus comprising:
   a ring structure configured to sit on a surface area of an eye, the ring structure having a top surface and a bottom surface, wherein the bottom surface is configured to touch the eye;
   a plurality of light-emitting elements configured in the ring structure;
   a plurality of apertures is configured on the bottom surface of the ring structure, wherein the plurality of light-emitting elements is aligned with the plurality of apertures;
   a non-transitory signal carrier running along at least a portion of the ring structure, the non-transitory signal carrier having one end configured to connect to a signal source and receive at least one of light and electricity from the signal source, and one or more opposite ends respectively coupled with the plurality of light-emitting elements; and
   one or more adjustable anterior segment lights positioned at one or more respective locations on an outer surface of the ring structure, the one or more adjustable anterior segment lights being coupled with the signal carrier, the signal carrier providing at least one of light and electricity used by the one or more adjustable anterior segment lights to provide additional illumination to the eye.

14. The apparatus of claim 13, wherein the bottom surface of the ring structure is configured as a curved or concave surface with each respective light-emitting end of the plurality of light-emitting elements facing away from the bottom surface of the ring structure.

15. The apparatus of claim 13, wherein the non-transitory signal carrier comprises an electrical cable, wherein the signal source comprises a power source, and wherein the plurality of light-emitting elements comprises light-emitting diodes (LEDs).

16. The apparatus of claim 13, wherein the signal source comprises at least one of a battery and a power supply.

17. The apparatus of claim 13, further comprising:
an illumination device extending from the top surface of the ring structure to provide additional illumination.

18. The apparatus of claim 17, wherein the illumination device is adjustable by a user to position the illumination device in a chosen direction.

\* \* \* \* \*